United States Patent [19]

Fischer et al.

[11] Patent Number: 5,863,977
[45] Date of Patent: *Jan. 26, 1999

[54] HIGH MOLECULAR WEIGHT S-EB-S HOT MELT ADHESIVE

[75] Inventors: Carolyn A. Fischer, Stillwater; Eugene R. Simmons, Vadnais Heights; Mark S. Kroll, Arden Hills; Jeffrey S. Lindquist, Cottage Grove, all of Minn.

[73] Assignee: H. B. Fuller Licensing & Financing, Inc., St. Paul, Minn.

[ * ] Notice: The term of this patent shall not extend beyond the expiration date of Pat. No. 5,459,193.

[21] Appl. No.: 798,808

[22] Filed: Feb. 12, 1997

Related U.S. Application Data

[60] Division of Ser. No. 525,238, Sep. 8, 1995, abandoned, which is a continuation-in-part of Ser. No. 393,242, Feb. 23, 1995, Pat. No. 5,459,193, which is a continuation of Ser. No. 134,933, Oct. 12, 1993, abandoned.

[51] Int. Cl.$^6$ .............................. C08L 9/06; C08L 53/02
[52] U.S. Cl. .............................. 524/505; 525/88; 525/98
[58] Field of Search ................ 525/88, 98; 524/505

[56] References Cited

U.S. PATENT DOCUMENTS

| | | | |
|---|---|---|---|
| 3,652,474 | 3/1972 | Berry et al. | 260/27 |
| 4,136,699 | 1/1979 | Collins | 128/290 R |
| 4,369,284 | 1/1983 | Chen | 524/476 |
| 4,411,058 | 10/1983 | Chen | 29/571 |
| 4,569,124 | 2/1986 | Rensch et al. | 29/591 |
| 4,618,213 | 10/1986 | Chen | 350/96.34 |
| 4,813,947 | 3/1989 | Korpman | 604/387 |
| 4,833,193 | 5/1989 | Sieverding | 524/486 |
| 5,085,655 | 2/1992 | Mann et al. | 604/389 |
| 5,149,741 | 9/1992 | Alper | 525/95 |
| 5,153,254 | 10/1992 | Chen | 524/505 |
| 5,204,390 | 4/1993 | Szymanski et al. | 524/91 |
| 5,239,723 | 8/1993 | Chen | 15/104.002 |
| 5,262,486 | 11/1993 | Chen | 524/476 |
| 5,559,165 | 9/1996 | Paul | 523/111 |

FOREIGN PATENT DOCUMENTS

| | | |
|---|---|---|
| 2049168 | 2/1992 | Canada . |
| 0 428 107 A2 | 5/1991 | European Pat. Off. . |
| 0428017 | 5/1991 | European Pat. Off. . |
| 0 471 384 A1 | 2/1992 | European Pat. Off. . |

OTHER PUBLICATIONS

What is KRATON® Rubber?

*Primary Examiner*—Irina Zemel
*Attorney, Agent, or Firm*—Carolyn A. Fischer; Nancy N. Quan

[57] ABSTRACT

This invention relates to hot melt adhesives comprising a high molecular weight polystyrene-ethylene/butylene-polystyrene block copolymer and articles constructed therefrom. This polymer is useful in a variety of hot melt adhesive applications such as food packaging adhesives, rodent traps, skin attachment adhesives, positioning adhesives, diaper tapes, low tack diaper fastening systems, foam in place gaskets, etc.

15 Claims, 1 Drawing Sheet

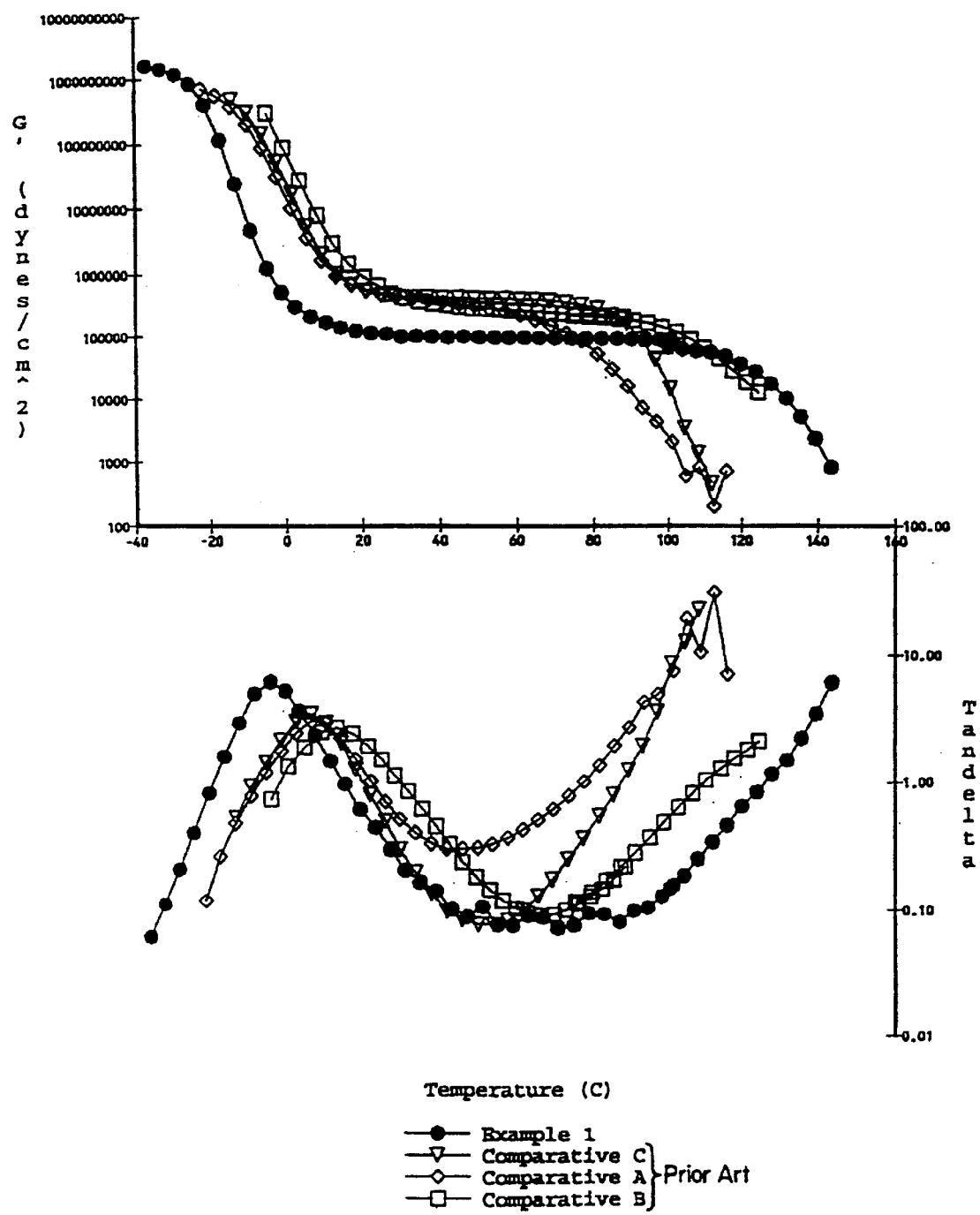

HIGH MOLECULAR WEIGHT S-EB-S HOT MELT ADHESIVE

REFERENCES TO RELATED APPLICATION

This application is divisional of Ser. No. 08/525,238, filed Sep. 8, 1995 which is a continuation-in-part of Ser. No. 08/393,242, filed Feb. 23, 1995, issued U.S. Pat. No. 5,459,193, which is a continuation of application Ser. No. 08/134,933, filed Oct. 12, 1993, abandoned.

FIELD OF THE INVENTION

This invention relates to hot melt adhesives comprising a high molecular weight polystyrene-ethylene/butylene-polystyrene block copolymer and articles constructed therefrom. This polymer is useful in a variety of hot melt adhesive applications such as food packaging adhesives, rodent traps, skin attachment adhesives, positioning adhesives, diaper tapes, low tack diaper fastening systems, foam in place gaskets, etc.

BACKGROUND OF THE INVENTION

Block copolymers have been used widely in the hot melt adhesive industry for a variety of applications. Block copolymers are often the preferred polymer base due to their good heat stability, high cohesive strength, and compatibility with a wide range of tackifiers and plasticizers.

Kraton G-1651, a S-EB-S linear A-B-A block copolymer, having a molecular weight of about 240,000, is intended for use by the injection molding industry for shoe soles. Due to its relatively high molecular weight, it was thought unsuitable for the hot melt adhesive industry.

Chen, U.S. Pat. No. 4,369,284 teaches dimensionally stable gelatinous elastomer compositions. Utility for such compositions include toys, therapeutic hand exercising grips, shock absorbers, acoustical insulators, and other uses. The essential ingredients of Chen consist of high styrene S-EB-S polymer in combination with high levels of plasticizing oil. Since such compositions do not include the use of tackifying resins, and that Chen teaches away from blending such polymers with other polymers, tackifiers, and fillers, such compositions are not useful as adhesives.

Sieverding, U.S. Pat. No. 4,833,193 claims the use of Kraton G-1651 alone or in combination with an ethylene-propylene diblock copolymer, at least 20% of a low molecular weight resin having a ring and ball softening point of about 10° C. to 45° C., and up to 80 weight percent of a mineral oil. Sieverding sets forth that an exceptional feature of his invention is the uniquely high concentration of low molecular weight resins. In the 196 examples set forth, Sieverding does not teach blending Kraton G-1651 with other block copolymers other than an ethylene-propylene diblock copolymer nor does he teach the use of solid tackifiers.

Conventional block copolymers are known and disclosed in various patents such as Collins, U.S. Pat. No. 4,136,699, Malcolm et al., U.S. Pat. No. 5,0547,571 and Raykovitz et al., U.S. Pat. No. 4,704,110.

SUMMARY OF THE INVENTION

The applicants have found that Kraton G-1651 can be used in a variety of applications where high cohesive strength and/or high tack is an important parameter. Furthermore, the applicants have found that incorporating Kraton G-1651 at very low concentrations can dramatically improve the heat resistance, cold temperature flexibility, and plasticizer staining resistance of a variety of adhesive formulations.

The present invention is a hot melt adhesive comprising:

(a) about 2.0 percent to about 20.0 percent by weight of an A-B-A block copolymer having a molecular weight greater than about 200,000, said block copolymer having polystyrene end blocks and a substantially saturated midblock;

(b) up to about 30 percent by weight of a compatible block copolymer;

(c) about 20 to 95 percent of a compatible liquid plasticizer;

(d) up to 60 percent by weight of a compatible solid tackifing agent.

Adhesive compositions exhibiting high tack in combination with high cohesive strength are useful in a variety of applications. Some adhesive formulations display unique adhesion to skin properties while other formulations exhibit low self peel properties which may eliminate the need for release paper on articles that incorporate such. Other applications that Kraton G-1651 adhesive compositions are useful for include, but are not limited to, diaper tapes, medical tapes, foamable gaskets, medical devices, freezer grade and heat resistant food packaging adhesives, rodent traps, waterproofing stitched seams for shoe assembly, tennis court surface repair, low tack fastening systems, removable and resealable adhesive applications, improved positioning adhesives for feminine napkins, elastic attachment adhesives, diaper construction adhesives, elastomeric compositions that could be used in place of spandex or natural rubber, etc.

BRIEF DESCRIPTION OF THE DRAWING

The drawing is a chart of rheology data from the prior art and the present invention.

DETAILED DESCRIPTION OF THE PREFERRED EMBODIMENT

The critical component of the adhesive of this invention, present in the amount of about 2.0% to about 20% by weight, comprises a substantially linear A-B-A block copolymer having a weight average molecular weight in excess of about 200,000 as measured by Gel Permeation Chromatography, with values reported relative to polystyrene standards; wherein said A block is polystyrene and said B block is ethylene-butylene, ethylene-propylene, or mixtures thereof. Polymers of this type, such as Kraton G-1651, are twice the molecular weight of conventional S-EB-S block copolymers intended for the hot melt adhesive industry. Therefore, typical technical information relating to adhesive performance properties is unknown.

The applicants have found that the above S-EB-S block copolymer may also have added thereto, a compatible A-B-A triblock copolymer, an A-B diblock copolymer, an A-B-A-B-A-B multiblock copolymer or radial block copolymer, and grafted versions of such including Shell Chemical's TKG-101 and RP-6912. Such A-B-A block polymers are disclosed in Collins et al., U.S. Pat. No. 4,136,699 or available under the tradename of Kraton G-1654 commercially available from Shell Corporation. We envision grafted modifications of Kraton G-1651 to exhibit even greater improvements in tack properties, although no such polymer structure has yet been manufactured. At small concentrations (less than about 4%) Kraton G-1651 may also be blended with other polymers such as EVA, EMA, as well as crystalline and amorphous polyolefins. The use of additional block copolymers is preferred if one desires to reduce the viscosity to improve the processability of the adhesive and/or increase the tack for some applications, but is not necessary to the invention.

Tackifying Resin

The adhesive of the invention contains a tackifying resin. Tackifying agents are present in amounts up to 90% by weight. Preferably, the resin is present in an amount of 20 to 60 weight percent. Tackifying resins useful in the adhesives of the invention comprise resins derived from renewable resources such as rosin derivatives including wood rosin, tall oil, gum rosin; rosin esters, natural and synthetic terpenes, and derivatives of such. Aliphatic, aromatic or mixed aliphatic-aromatic petroleum based tackifiers are also useful in the adhesive of this invention. Representative examples of useful hydrocarbon resins includes alpha-methyl styrene resins, branched and unbranched $C_5$ resins, $C_9$ resins, $C_{10}$ resins, as well as styrenic and hydrogenated modifications of such. The article by Davis, "The Chemistry of $C_5$ Resin," discusses synthetic $C_5$ resin technology. Tackifying resins range from being a liquid at 37° C. to having a ring and ball softening point of about 135° C. A preferred tackifying agent is a hydrogenated $C_{10}$ resin.

Plasticizers

A plasticizer is broadly defined as a typically organic composition that can be added to thermoplastics, rubbers and other resins to improve extrudability, flexibility, workability, or stetchability. A minimum amount of fluid ingredient is necessary to the present invention. Such fluid ingredient may be provided as a plasticizer, a liquid resin, a liquid elastomer or any other material which flows at ambient temperatures.

Plasticizers are used in the adhesive of this invention. Preferably the plasticizing agent is a liquid at ambient temperature, such as hydrocarbon oils, polybutene, liquid tackifying resins, liquid elastomers, and is present in amounts up to 95% by weight of the adhesive. Such oils are primarily hydrocarbon oils, low in aromatic content and are paraffinic or napthenic in character. The oils are preferably low in volatility, transparent and have as little color and odor as possible. The use of plasticizers in this inventions also contemplates the use of olefin oligomers, low molecular weight polymers, vegetable oils and their derivatives and similar plasticizing liquids.

As is known in the art, various other components can be added to modify the tack, color, odor, etc., of a hot melt adhesive. It is generally preferred that the other components or ingredients should be relatively inert and have negligible effects upon the properties contributed by the block copolymer, tackifying agent, and plasticizing oil. Antioxidants and other stabilizing ingredients can also be added to protect the adhesive from various heat and light induced degradation, but are not essential to the compositions of this invention.

| Adhesives | Useful for Hot Melts |
|---|---|
| Kraton G-1651 | 2.0 – 20 |
| Compatible Block Copolymer | 0 – 30 |
| Solid Tackifier | 0 – 60 |
| Liquid Tackifier/Plasticizing Oil | 20 – 95 |

TEST METHODS

T-peels

This test method describes how to measure the removal force of an adhesive surface bonded to itself or a fabric substrate.

Material and Equipment:
1. Mechanical roll-down device with 4½ lb. roller.
   Available through: Engineering Service, Glenview Ill. 60025

2. Slip Peel Tester
   Available though: Instrumentors, Inc., Cleveland, Ohio 44136

The first step is to prepare hot melt coated adhesive films on Mylar or polyethylene film using a suitable coating device at an appropriate application temperature. During preparation of the adhesive film, the adhesive surface is covered with release paper to facilitate handling. The coat weight is checked targeting 50 g/m2+/−3 g/m2.

The adhesive coated mylar is cut into 1" and 1.5" width strips 4 inches in length in machine direction. At one end of each strip, fold approximately ¼" of the strip onto itself to create a grip. Remove the release paper and place the adhesive surface of one 1" wide strip onto the adhesive surface of one 1.5" strip with the grips at the same end. Place the composite on the mechanical roll-down device, and allow the roller two passes over the sample, one forward and one back. A timer is activated and the sample is placed into the jaws of the slip-peel tester. The 1" wide strip is placed into the mobile jaw and the 1.5" strip in the stationary jaw. No more than 1 minute after the sample has been removed from the roll-down device, the sample is peeled at 12 inches per minute, averaging over 10 seconds. The procedure is repeated five time, recording the average T-peel value and noting any legging or transfer. The T-peel values are reported in grams per lineal inch. For the laminate peel test, the samples are rolled-down, placed in an envelope and conditioned at 120° F. and 50% relative humidity for one week. The samples are then removed from the oven, allowed to equilibrate to room temperature and then peeled in the manner described above.

The same method is followed for the initial T-peel to cotton and nylon test with the exception that the adhesive surface of the 1" wide mylar strip is put in contact with a knit cotton or Tricot nylon fabric. The delayed T-peel to cotton differs from the initial T-peel to cotton in that the composite is placed on the bench top for 105 minutes after being rolled-down prior to peeling.

In the disposable article industry, it is preferred to have an initial T-peel to cotton in the 100–500 g range, most preferred 200–500 g. In order to achieve preferred stay-in-place properties, the initial T-peel value should be approximately equal to the delayed T-peel, indicating no loss of adhesion over time under conditions of low stress.

With regard to the self peel, it is preferred to have a value less than 200 g, most preferred less than about 100 g. Values greater than 200 g often result in substrate or backing failure of the article.

Creep

This procedure covers the method for applying and testing adhesives for multi-strand elastic attachment.

Adjust the hot melt applicator and laminator to proper setting.

| Temperature: | 300° F. |
|---|---|
| Nip Pressure | 30 psi |
| Application Rate | 15 mg/sq. in. |
| Web Speed | 400–500 ft/min |
| Elongation | 200–300% |

Spray the adhesive through 4 strands of Lycra® to treated polyethylene nipping the bond to nonwoven substrate. The height of the nozzle should be adjusted to allow the air volume to be as high as possible to achieve the most wrapping of the adhesive around the elastic without overspray. To determine the creep resistance, the laminate construction is secured to a rigid sheet of cardboard at 95% of the original length of the polyethylene substrate. Cut through the individual strands of elastic such that each strand is able to move freely within the lamination. Condition the board for 4 hours at 100° F. marking the polyethylene where the elastic is still bonded at 1 and 4 hours, represented by the gathered portion of the lamination. Determine the percent creep of each lamination, reporting the average of five.

Fineline & Spray

Prepare fineline and spray bonds using the same settings as the creep test at application rates of 1.4 mg/linear in. for fineline bonds and 4 mg/sq. in. for spiral spray. During the run, drop eight to ten 2"×8" strips of release paper cross directional across the web to serve as starting points for the T-peel evaluation. Cut 10 samples one bead or one spray spiral in width by 3" in length. Run T-peels on a slip/peel tester, Instron or other suitable measuring device at 12"/min. Report the average of 10 samples.

Stain Resistance

The adhesive is coated onto polyester film at a coating weight of 25 g/M$^2$. A square of adhesive coated film having an area of approximately 1300 mm$^2$ is then adhered to standard 50#/ream high speed copy paper such as Basics #01811 distributed by Basicnet Inc. The samples are then put in a 120° F. oven for 96 hours. A concentric stain forms around each sample on the paper. The size of the stain is indicative of the plasticizer staining tendencies.

EXAMPLES 1–13

The following examples were made using a sigma blade mixer with standard hot melt blending techniques and tested in accordance with the test methods described above.

Improved Positioning Adhesive

A positioning adhesive is typically pressure sensitive in nature and is sandwiched between the garment facing surface of a feminine napkin and release paper. Upon use, the release paper is removed and the napkin is secured to an undergarment by means of the positioning adhesive.

FIG. 1 illustrates one of the advantageous features the present invention exhibits over prior art. Comparative Examples A, B, and C, of which their compositions are depicted in Table 1, are representative of the prior art and are standard positioning adhesives of the industry. Example 1 is an improved positioning adhesive of the present invention. The composition of Example 1 is depicted in Table 3. The prior art exhibits a balance of tack and shear strength such that they exhibit a high modulus at room temperature in order to possess adequate cohesive strength. (G', G" crossover 80° C. to 100° C.). Surprisingly, the present invention exhibits a lower G' at room temperature indicative of better wetting properties while simultaneously exhibiting higher cohesive strength indicated by a crossover point of 110° C. and above. Thus, adhesives of the present invention exhibit both high tack and high cohesive strength compared to prior art adhesives which generally exhibit a compromise of tack and cohesive strength.

Examples 1, 2 and 3 of Table 3 represent improved positioning adhesives, of the present invention for a disposable article, such as a feminine napkin. Examples 1, 2 and 3 exhibit excellent stay in place properties as depicted by the delayed T-peels being approximately equal to the initial T-peels in Table 2. Examples 1 and 2 also exhibits low self adhesion properties which is advantageous as a wing adhesive or for manufacturing release paper free pressure sensitive articles. Details concerning the advantages of low self T-peels are explained in the applicants' parent application Ser. No. 08/134,933, filed Oct. 12, 1993, which has been allowed, incorporated herein by reference. The applicants anticipate utilizing Kraton G-1651 in a screen printable positioning adhesive which would exhibit comparable tack properties to slot coat applications at drastically reduced coating weights.

Multipurpose Elastic Attachment Adhesive

Example 4 of Table 3 represents a multipurpose elastic attachment adhesive useful for various disposable articles such as disposable diapers. Following is data comparing Example 4 to a representative example from Alper et al., U.S. Pat. No. 5,149,741 of which the composition is depicted in Table 1. Kraton G based products are typically not used for multipurpose elastic attachment type products.

| Hour Creep | Construction T-peels | 1 Hour Creep |
|---|---|---|
| Example 4 17% | 130 g +/− 15 | 13% |
| Comparative D 75% | 187 g +/− 19 | 47% |

Low Tack Fastening System

Example 5 represents a cohesive cold seal adhesive composition having utility in a variety of applications to replace tape and velcro fastening systems for disposable diapers and other articles that incorporate such. Cohesive cold seal adhesive compositions are typically coated or heat welded to a select substrate. Once cooled to room temperature, the adhesive will bond or seal only to itself or a similarly coated surface or substrate.

Rodent Trap Adhesive

Example 6 represents a rodent trap adhesive which is a substantial cost savings relative to existing technology. The adhesive composition covers the bottom surface of a container such as box and is subsequently baited to form a trap. Often an additive is incorporated directly into the adhesive which attract rodents and eliminates the need for bait. The adhesive exhibits high tack and cohesive strength such that once a rodent becomes adhered to the adhesive, it is unable to free itself.

Extrudable Resealable Film

Example 7 represents a useful extrudable film. The adhesive is blown in line, sandwiched between two layers of film. This laminate is useful for the manufacture of resealable food packages. Adhesive compositions useful for extruder film blowing application must be very high in viscosity while providing a soft resealable closure. The adhesive compositions are designed to fail cohesively, thus providing a self-seal. Blending Kraton G-1651 with conventional G polymers such as Kraton G-1657 and Kraton G-1650 also provides suitable compositions for this use.

Improved Stain Resistance

Examples 8–11 of Table 4 represent the use of Kraton G-1651 to improve the stain resistance of a pressure sensitive adhesive. Small concentrations of Kraton G-1651 reduce the bleeding tendencies without adversely affecting the adhesive properties. Following is a data depicting the improvement in bleeding tendencies due to the presence of small concentrations of G-1651. The control sample comprises 10% Kraton G-1652 and 90% oil.

| Staining Reduction | Stain Area | % |
|---|---|---|
| Control | 16,700 mm$^2$ | — |
| Example 8 | 10,390 | 38% |
| Example 9 | 7,090 | 58% |
| Example 10 | 5,540 | 67% |
| Example 11 | 4,300 | 74% |

Skin Attachment Adhesive

Examples 2, 12 and 13 represent the use of Kraton G-1651 in an improved skin attachment adhesive for medical devices. The skin attachment adhesives set forth in Sieverding are very aggressive at high removal rates which may cause irritation.

TABLE 1

| Ingredient | Tradename | Percent by Weight |
|---|---|---|
| Comparative A (Raykovitz et al., U.S. Pat. No. 4,704,110) | | |
| A-B-A Block Copolymer | Stereon 840A | 30.0 |
| Plasticizing Oil | 500 Second Oil | 20.0 |
| Tackifying Resin | Zonatac 105 Lite | 49.5 |
| Antioxidant | Irganox 1010 | 0.5 |
| Comparative B (Collins et al., U.S. Pat. No. 4,136,099) | | |
| A-B-A Block Copolymer | Kraton G-1650 | 15.3 |
| Plasticizing Oil | 1200 Second Oil | 28.0 |
| Tackifying Resin | Wingtack 95 | 53.5 |
| Antioxidant | Irganox 1010 | .1 |
| Antioxidant | Irganox 1076 | .1 |
| Pigment | PMS-04110-PHM | 3.0 |
| Comparative C (Nelson et al., U.S. Pat. No. 0,525,251) | | |
| A-B-A Block Copolymer | Vector 4411 | 30.0 |
| Plasticizing Oil | Kaydol Oil | 20.0 |
| Tackifying Resin | Zonatac 105 Lite | 49.0 |
| Antioxidant | Irganox 1010 | 1.0 |
| Comparative D (U.S. Pat. No. 5,149,741) | | |
| A-B-A Block Copolymer | Sol T-193B | 24.8% |
| Tackifying Resin | Bevelite 62-107 | 59.7 |
| Plasticizing Oil | Kaydol | 15.0 |
| Antioxidant | Irganox 1010 | .5 |

TABLE 2

All samples were manufactured with standard hot melt blending techniques.

| | Comparative "A" | Comparative "B" | Comparative "C" | Example 1 | Example 2 | Example 3 |
|---|---|---|---|---|---|---|
| Initial T-peel to Cotton | 526 +/- 52 | 452 +/- 44 | 192 +/- 13 | 219 +/- 34 | 291 +/- 19 | 560 +/- 18 |
| Delayed T-peel to Cotton | 522 +/- 39 | 277 +/- 17 | 135 +/- 18 | 297 +/- 6 | 290 +/- 19 | 579 +/- 57 |
| Initial T-peel to Nylon | 806 +/- 111 | 526 +/- 47 | 456 +/- 37 | 287 +/- 21 | 251 +/- 25 | 329 +/- 35 |
| Self T-peel | 523 +/- 24 | 702 +/- 65 | 390 +/- 27 | 46 +/- 5 | 62 +/- 6 | — |
| Laminate T-peel | * | * | * | 95 +/- 5 | 124 +/- 2 | — |
| Viscosity @ 300° F. | 12,375 cps | 17,000 cps | 4,720 cps | 23,500 cps | 9,000 cps | 27,000 cps |
| Viscosity @ 325° F. | 7,375 | 4,500 | 2,730 | 6,500 | 3,525 | 10,500 |
| Viscosity @ 350° F. | 4,840 | 1,850 | 1,365 | 3,000 | 1,910 | 5,375 |

*The laminate T-peel was not tested on the comparative samples because the self T-peel values were greater than 200 g.

TABLE 3

| Ingredient (Tradename) | Example 1 | Example 2 | Example 3 | Example 4 | Example 5 | Example 6 | Example 7 |
|---|---|---|---|---|---|---|---|
| Kraton G-1651 | 10.0% | 6.0 | 11.1 | 9.6 | 7.0 | 4.0 | 10.0 |
| Kraton G-1654 | — | 4.0 | — | — | — | — | — |
| Kraton G-1650 | — | — | — | — | 17.1 | 10.0 | 10.0 |
| Kraton G-1726 | — | — | — | — | — | — | — |
| Kraton G-1652 | — | — | — | 2.4 | — | — | — |
| Escorez 5380 | 49.8 | 49.8 | — | — | — | — | — |
| ECR-177 | — | — | 36.5 | 63.0 | — | — | — |
| Regalrez 1018 | — | — | 31.4 | — | — | — | — |
| Wingtack Extra | — | — | — | — | — | 50.0 | — |
| Zonarez 7115 | — | — | — | — | — | — | 44.3 |
| 500 Oil | 40.0 | 40.0 | 20.8 | 24.8 | — | — | — |
| 2000 Oil | — | — | — | — | — | 45.5 | — |
| Kaydol | — | — | — | — | 75.9 | — | 35.0 |
| Irganox 1010 | .1 | .1 | .2 | .5 | .5 | .5 | .5 |
| Irganox 1076 | .1 | .1 | .2 | — | — | — | — |

TABLE 4

| Ingredient (Tradename) | Example 8 | Example 9 | Example 10 | Example 11 | Example 12 | Example 13 |
|---|---|---|---|---|---|---|
| Kraton G-1651 | 2.0% | 2.5% | 3.0% | 4.0% | 8.0% | 7.5% |
| Kraton G-1652 | 8.0 | 7.5 | 7.0 | 6.0 | — | — |
| Kraton G-1726 | — | — | — | — | 4.0 | 7.5 |
| Esaorez 5380 | — | — | — | — | 20.0 | 42.5 |
| Regalrez 1018 | — | — | — | — | 27.8 | — |
| Kaydol | 35.0 | 35.0 | 35.0 | 35.0 | 40.0 | 35.0 |
| Irganox 1010 | — | — | — | — | 0.2 | 0.5 |

The above specification, examples and data provide a complete description of the manufacture and use of the composition of the invention. Since many embodiments of the invention can be made without departing from the spirit and scope of the invention, the invention resides in the claims hereinafter appended.

We claim:

1. A disposable article having a fastening system coated with an adhesive composition comprising:

(a) about 2 to about 20 percent by weight of an A-B-A block copolymer having a molecular weight greater than about 200,000; said block copolymer having polystyrene end blocks and a substantially saturated midblock;

(b) about 20 to 95 percent by weight of a compatible liquid ingredient; and (c) up to about 60 percent by weight of at least one tackifier.

2. The disposable article of claim 1 wherein the block copolymer of the adhesive composition comprises an A block of polystyrene and a B block selected from the group consisting of ethylene-butylene, ethylene-propylene, and mixtures thereof.

3. The disposable article of claim 1 wherein the adhesive composition further comprises from about 4 to about 30 percent by weight of a second compatible block copolymer.

4. The disposable article of claim 1 wherein at least one tackifier of said adhesive composition is a solid at ambient temperature.

5. The disposable article of claim 1 wherein said article is selected from the group consisting of tapes, sanitary napkins, disposable diapers and medical devices.

6. The disposable article of claim 1 wherein said article further comprises at least one absorbent.

7. A medical device coated with an adhesive composition for securing the device to skin; said adhesive composition comprising:

(a) about 2 to about 20 percent by weight of an A-B-A block copolymer having a molecular weight greater than about 200,000; said block copolymer having polystyrene end blocks and a substantially saturated midblock;

(b) about 20 to 95 percent by weight of a compatible liquid ingredient; and (c) up to about 60 percent by weight of at least one tackifier.

8. The medical device of claim 7 wherein the block copolymer of the adhesive composition comprises an A block of polystyrene and a B block selected from the group consisting of ethylene-buytlene, ethylene-propylene, and mixtures thereof.

9. The medical device of claim 7 wherein the adhesive composition further comprises from about 4 to about 30 percent by weight of a second compatible block copolymer.

10. The medical device of claim 7 wherein at least one tackifier of said adhesive composition is a solid at ambient temperature.

11. A package having a closure system coated with an adhesive composition comprising:

(a) about 2 to about 20 percent by weight of an A-B-A block copolymer having a molecular weight greater than about 200,000; said block copolymer having polystyrene end blocks and a substantially saturated midblock;

(b) about 20 to 95 percent by weight of a compatible liquid ingredient; and (c) up to about 60 percent by weight of at least one tackifier.

12. The package of claim 11 wherein the block copolymer of the adhesive composition comprises an A block of polystyrene and a B block selected from the group consisting of ethylene-butylene, ethylene-propylene, and mixtures thereof.

13. The package of claim 11 wherein the adhesive composition further comprises from about 4 to about 30 percent by weight of a second compatible block copolymer.

14. The package of claim 11 wherein at least one tackifier of said adhesive composition is a solid at ambient temperature.

15. The package of claim 11 wherein said closure system is resealable.

* * * * *